United States Patent [19]

Santy

[11] 4,299,210
[45] Nov. 10, 1981

[54] UNIVERSAL SPLINT

[76] Inventor: James L. Santy, Box 783, 1362 Woodside Ave., Park City, Utah 84060

[21] Appl. No.: 164,910

[22] Filed: Jul. 1, 1980

[51] Int. Cl.³ .......................... A61B 17/18; A61F 5/04
[52] U.S. Cl. .................................... 128/87 R; 128/88; 128/90
[58] Field of Search ............... 128/77, 87 R, 83, 87 C, 128/88, 89 R, 90

[56] References Cited

U.S. PATENT DOCUMENTS

| | | | |
|---|---|---|---|
| 1,257,297 | 2/1918 | Brown | 128/88 |
| 1,639,815 | 8/1927 | Siebrandt | 128/88 |
| 2,947,306 | 8/1960 | Culkin | 128/88 |
| 3,439,672 | 4/1969 | Fisher | 128/88 |
| 4,050,456 | 9/1977 | Cornue | 128/88 |
| 4,259,950 | 4/1981 | Klippel | 128/89 R |

*Primary Examiner*—Robert W. Michell
*Assistant Examiner*—C. W. Shedd
*Attorney, Agent, or Firm*—M. Reid Russell

[57] ABSTRACT

The present invention in an improved universal splint is intended for use to immobilize a body extremity or extremities. The splint consists of a board arranged for attachment by straps, or the like, to a person's trunk area and an extremity support member pivotally connected thereto, made up of pivotally and hinge connected plates and support boards to provide for forming that support member to conform to an injured extremity, which extremity support member can be moved across the backboard to support either right or left side extremities. The hinge connections are preferably single hinges that can be locked independently and are each constructed to provide nearly three hundred sixty degrees (360°) arc of travel. The improved splint further includes a bar locking capability across the hinges to further rigidize the support member. The extremity support member is preferably foldable against the back board and includes appropriate strap connectors for releasably connecting it to a body extremity.

15 Claims, 9 Drawing Figures

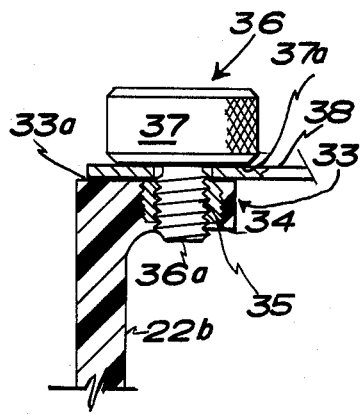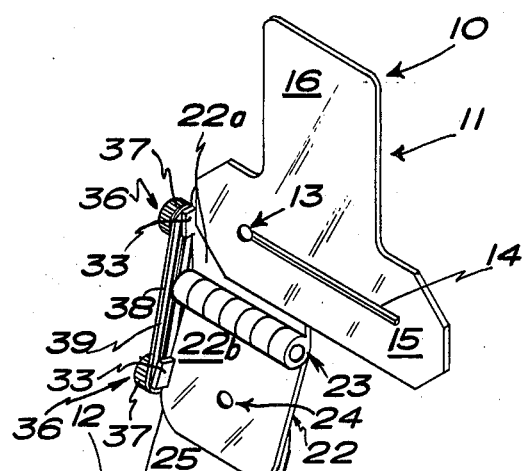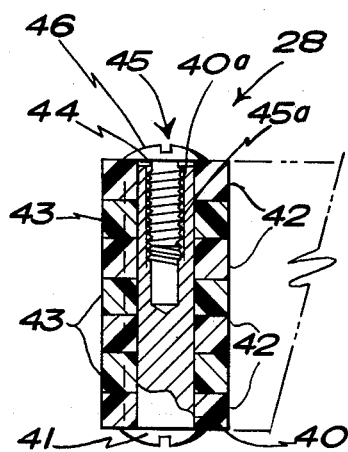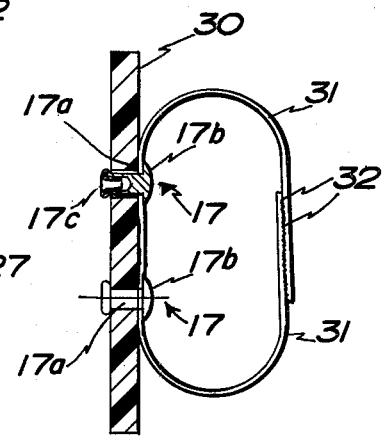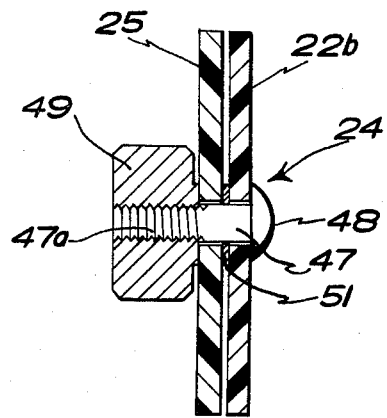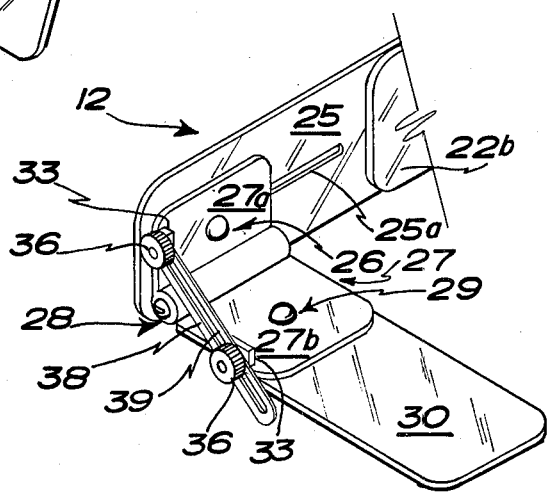

UNIVERSAL SPLINT

The present invention relates to splint devices for immobilizing a person's extremity or extremities.

Devices and arrangements for immobilizing or holding still injured body members or parts of a person's anatomy are, of course, well known and in common every-day usage. Examples of such devices are shown in early application for United States Letters Patent by the present inventor, in a Universal Splint, assigned Ser. No. 098,672. This device, along with earlier immobilizing devices cited therein, shows varied arrangements for use in conjunction with rendering emergency medical treatment. The earlier universal splint of the present inventor, like the present invention in an improved universal splint, provides for immobilizing any of the extremities, either legs, arms or head. Distinct from this earlier universal splint, however, the present invention employs a single hinge that includes both hinge compression and bar locking arrangements therewith to provide an extremely reliable extremity support member locking. Further, the present invention employs improved pivot couplings that, along with the hinges, connect together support boards and first and second plates into a more versatile extremity support member for splinting in place an injured body extremity.

It is, therefore, a general object of the present invention in an improved universal splint to provide a splint that includes an adjustable extremity support member pivotally connected thereto that can be easily conformed and locked in place.

It is an additional object of the present invention in an improved universal splint to provide as an extremity support member separate boards and plates that are connected by single hinge and pivot arrangements, which hinge and pivot arrangements can be individually locked in place.

It is an additional object of the present invention in an improved universal splint to provide for convenient length adjustment of the extremity support member, and to include fasteners therewith for easily securing both the back board and the extremity support member connected across a person's trunk and to an injured body extremity.

It is an additional object of the present invention to provide an improved universal splint that includes at least one extremity support member that can be arranged for immobilizing any body extremity.

In accordance with the above objects, the present invention in an improved universal splint should be understood to preferably include a back board that incorporates fasteners, belts, or the like, that are preferably formed from or have velcro strip ends, or the like, for securing the back board to a human torso. The back board is preferably contoured to fit comfortably across either the hips or the shoulder areas to provide a rigid anchor support for an extremity support member that is pivotally connected thereto. The pivot connection of the extremity support member is preferably arranged to travel freely in a transverse elongate groove formed across the back board and is capable of being locked at any point therealong, allowing the extremity support member to be used to support either side extremity or to be centered and folded appropriately to support a person's head.

To connect the extremity support member to the back board, a locking pivot coupling of a first plate of an upper hinge unit thereof is arranged in the transverse elongate opening formed across the back board allowing for travel of that pivot coupling and extremity support member across the back board. A single hinge connects the first plate to a second plate of the upper hinge unit, which hinge preferably includes both hinge compression locking and bar lock arrangement therewith for maintaining in place the plates of the upper hinge unit.

An upper extremity board is, in turn, pivotally connected by a locking pivot coupling to the second plate of the upper hinge unit. The above described arrangement and relationship of the back board, upper hinge unit and upper extremity board thereby provides for essentially an unlimited freedom of movement of these components to move said upper extremity board to the attitude of a person's injured extremity.

A second set of first and second hinge connected plates makes up a lower hinge unit. A first plate thereof is pivotally coupled to the above described upper extremity board and the second plate is pivotally connected to a lower extremity board. Like the back board, the lower extremity board and, as required, the upper extremity board, preferably include strips, belts, ties, or the like, for securing those boards to the person's injured extremity. The pivotal couplings of the lower hinge unit are preferably also capable, as is the hinge coupling thereof, of being locked in place, to conform the lower extremity board to the attitude of the lower part of the person's injured extremity and to lock in place for splinting that injured extremity.

The preferred back board can be attached across a person's shoulders or reversed and attached across their lower trunk area. Thereby, by moving the pivot coupling of the first plate of the upper hinge unit in the elongate opening across the back board, either a right or left side extremity can be supported. Further, the upper extremity board is arranged to be capable of telescoping outwardly, adjusting to the extremity to be splinted. Also, a second extremity support member can be installed in the transverse elongate opening formed in the back board to provide thereby for simultaneously splinting two arms or legs and, of course, two universal splint back boards could simultaneously be installed across a person's shoulders and lower trunk area.

FIG. 4, is another view of the improved universal splint of FIG. 1 showing the back board portion thereof rotated through approximately one hundred eighty degrees (180°) to illustrate that the back board can be arranged across a person's lower torso for immobilizing a leg;

FIG. 5, is a view of a portion of the lower extremity board and a lower hinge unit of the extremity support member to further illustrate the versatile adjustment capabilities thereof;

FIG. 6, is a sectional view taken along the line 6—6 of FIG. 1 showing a preferred hinge bar lock therefor as including a large headed bolt arranged for manual turning into a metal bushing in a post secured to the second hinge plates for sandwiching a locking bar therebetween for providing a bar lock across the hinge;

FIG. 7, is a sectional view taken along the line 7—7 of FIG. 1 showing a preferred locking hinge configuration;

FIG. 8, is a sectional view taken along the line 8—8 of FIG. 2 showing a preferred locking pivot connection arrangement of the present invention; and FIG. 9, is a sectional view taken along the line 9—9 of FIG. 2, showing straps with velcro strip ends as having been joined together for maintaining lower extremity board to the lower segment of a person's extremity, not shown.

Figure 1:
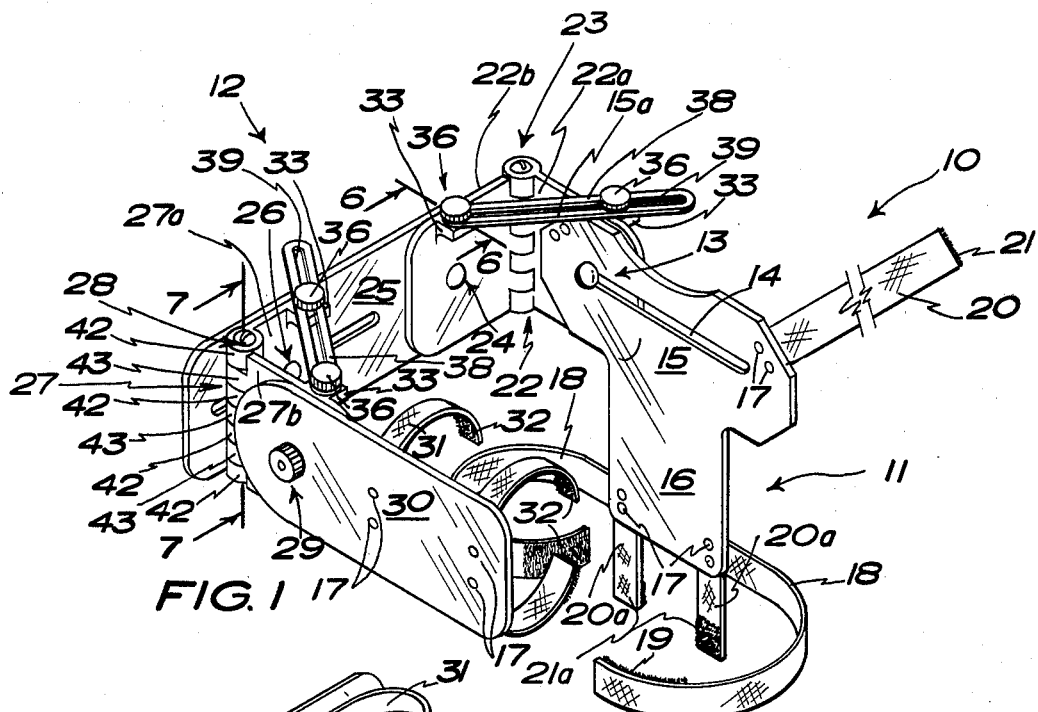
FIG. 1, is a profile perspective view of a preferred embodiment of an improved universal splint of the present invention shown as including ties with velcro strip ends arranged with a back board and a lower extremity board for attachment to a person.
Figure 2:
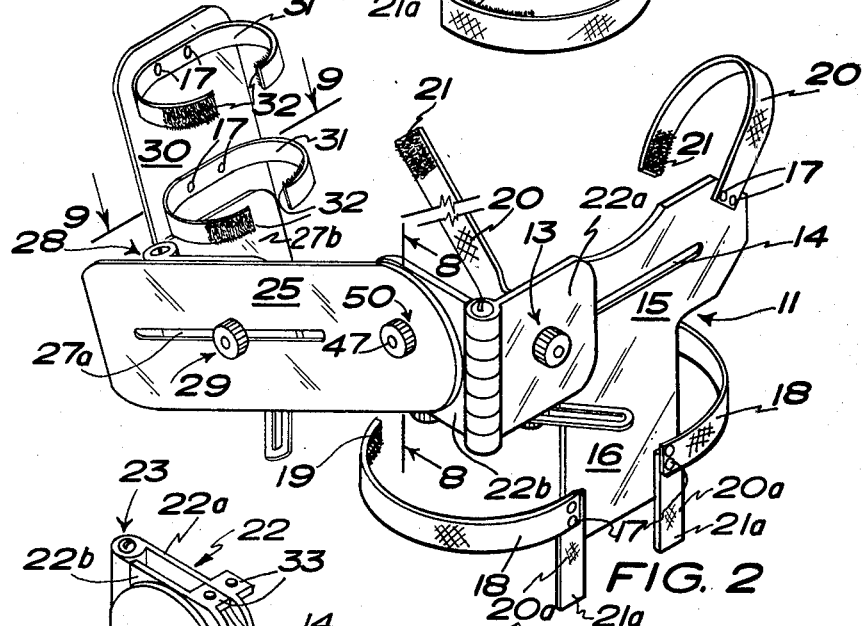
FIG. 2, is a rear perspective view of the improved universal splint of FIG. 1 showing the lower extremity board pivoted through approximately ninety degrees (90°)

In FIG. 1 is shown a profile perspective view of a preferred embodiment of an improved universal splint 10 of the present invention hereinafter referred to as a "splint 10". Shown therein the splint 10 preferably consists of a back board 11 whereto is pivotally connected, at back board pivot coupling 13, an extremity support member 12. Back board pivot coupling 13, hereinafter referred to as "back board pivot", is arranged to travel in a transverse elongate opening 14 that is formed across a top portion 15 of back board 11. Thereby the extremity support member 12 is free to travel across the back board 11 to support either a right or left side extremity. The back board is preferably formed to be wider at the top portion 15, and has a narrower bottom or tail portion 16. At the opposite sides of the tail portion 16 are attached straps 18, by rivets 17, or like fastening devices that, as shown in FIG. 2, each preferably include velcro strips 19 on the ends thereof. Straps 18 function as a waist belt by joining the velcro strips 19 with the back board top portion 15 thereby positioned across a person's shoulders or, as shown in FIG. 4, the back board can be rotated, the top portion 15 thereby spanning a person's lower torso. The back board top portion 15 is thereby preferably formed to fit comfortably across a person's shoulders or hips. With the back board top portion arranged across the person's shoulders, cross straps 20, that are maintained to that top portion 15 by rivets 17, that also preferably include velcro strip ends 21, can be arranged to cross the person's end connecting the straps 20a by joining velcro strip ends 21 and 21a thereof. So arranged, back board 11 can be easily joined to a person's torso with belt straps 18 and cross straps 20 and 20a or, as illustrated by FIG. 4, the back board 11 can be turned one hundred eighty degrees (180°) for attachment across a person's buttocks area, the cross straps 21 and 20a then serving as crotch straps.

As shown best in FIGS. 1, 2 and 4, a preferred arrangement of the extremity support member 12 includes first plate 22a and second plate 22b that make up an upper hinge unit 22, which plates are connected by single hinge 23 along edges thereof. First plate 22a includes back board pivot 13 that is arranged in the transverse elongate opening 14 of back board 11, and the second plate 22b includes a pivot 24 for pivotal connection to one end of an upper extremity board 25. Upper extremity board 25 is arranged to be length adjustable, as will be explained hereinafter, to conform to, for attachment to and support of, an upper arm or thigh area, an arm or leg.

The other end of the upper extremity board 25 is, in turn, pivotally coupled by a sliding pivot 26, to a first plate 27a of a lower hinge unit 27. First plate 27a is connected along one edge by a hinge 28 to an edge of a second plate 27b, which lower plate 27b, is in turn, connected by a pivot 29 to a lower extremity board 30. Lower extremity board 30, it should be understood, is intended to be arranged to support the forearm or calf area of a person's arm or leg and can be attached thereto by straps 31, as shown in FIGS. 1 and 2, that, like the described straps 18, 20 and 20a are secured to the boards by rivets 17 and preferably include velcro strip ends 32 for connecting the straps around the person's forearm or calf, holding it thereto. As shown in FIG. 4, the sliding pivot 26 is arranged in a centered longitudinal opening 25a formed in upper extremity board 25 for providing a spacing adjustment capability between upper and lower hinge units 22 and 27.

Shown in FIG. 1, the hinge connected first and second plates 22a, 22b and 27a and 27b, preferably all include bar lock arrangements that extend between the plates. The preferred bar locking arrangement, as shown therein, include tabs 33, one end on each plate, that extend at approximately normal angles inwardly from faces of plates 22a, 22b, 27a and 27b at coplanar edges thereof. As shown best in FIG. 6, each tab 33 has a hole 34 formed therethrough that can be individually threaded or, preferably, incorporates a threaded bushing 35 installed therein. Threaded bushing 35, as shown in FIG. 6, preferably receives a bolt 36 turned therein, which bolt 36 has a threaded shaft 36a and incorporates a large head 37, to facilitate its being manually turned. In operation, the under surface 37a of head 37, when shaft 36a of bolt 36 is turned appropriately into bushing 35, will engage a top surface of a bar 38, as shown best in FIGS. 1 and 6, to press that bar against a top surface 33a of tab 33 to provide for a friction lock therebetween. Bar 38, as shown best in FIG. 1, includes a center longitudinal opening 39 therein wherethrough shafts 36a of bolts 36 are turned into bushings 35. Thereby, with each bolt 36 turned, as described, bar 38 is sandwiched between the undersurfaces 37a of heads 37 and tab top faces 33a between tabs 33 to provide friction locking thereto, the bar 28 spanning across hinges 23 and 28, locking in place the first and second plates 22a, 22b, 27a and 27b of upper and lower hinge units 22 and 27.

To provide for additional hinge locking, as shown best in FIG. 7, hinges 23 and 28 each consist of hinge halves that include fingers 42 and 43, respectively, that will align and interdigitate the fingers including holes therethrough that align when the hinge halves are appropriately interdigitated. So arranged, a sleeve 40 can be asserted through the aligned holes that is open at end 40a opposite to a head end 41 thereof and is internally threaded at 44 to accommodate a bolt 45 that has a threaded body 45a turned therein. Bolt 45, as shown best in FIG. 7, preferably includes a notched head 46, or, alternatively, sleeve head 41 and bolt head 35 could be of sufficient diameter to accommodate a manual turning thereof within the scope of this disclosure. So arranged, by appropriately fitting a tool, such as a screw driver, not shown, into the notches of sleeve and bolt heads 41 and 46, respectively, and turning appropriately the sleeve 40 and/or bolt 45, the fingers 42 and 43 will be compressed together providing a friction lock. The present invention thereby, preferably provides for both locking together of the fingers of the individual hinges 23 and 28 and a locking with bar 38 across the hinges between the respective first and second plates 22a, 22b, 27a and 27b of the hinge units.

Additional to the above described hinge locking, to provide for rigidizing the extremity support member 12 from back board 11, the described pivot couplings for linking the plates and boards of the extremity support member together and back board pivot 13 are all, preferably, capable of locking. Therefore, the preferred pivots or pivot couplings, it should be understood, are identical and therefore, a description of one pivot coupling should be taken as a description of the others also. Shown in FIG. 8 is a profile sectional view of a preferred pivot coupling 24 for joining second plate 22b of the upper hinge unit 22 to upper extremity board 25. Pivot coupling 24 is shown therein as including a bolt 47 that incorporates a round head 48 on one end thereof, has a threaded body 47a and is turned into a nut 49. Nut 49, preferably has a knurled surface to facilitate its being manually turned by an operator, not shown. Turning of nut 49 on bolt 47 presses together second plate 22b and upper extremity board 25 surfaces to increase friction forces therebetween. To further increase friction forces between the surfaces, these surfaces could be scored or grooved appropriately, not shown, and/or washer 51, as shown in FIG. 8, could be included.

Figure 3:
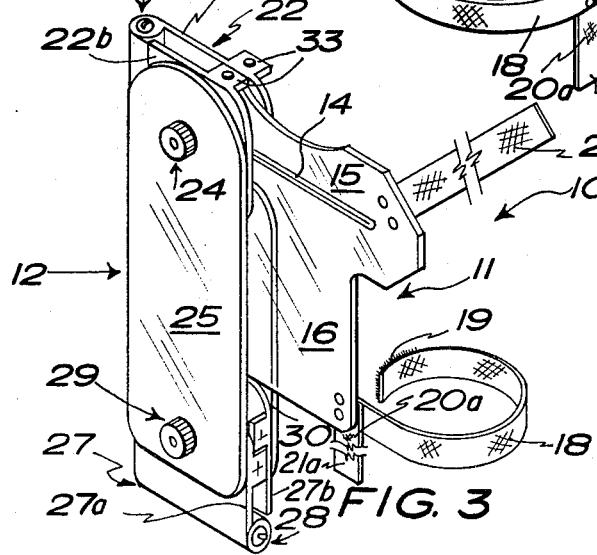
FIG. 3, is a view of the back board of the improved universal splint of FIG. 1 showing an extremity support member thereof that includes the lower extremity board, folded and pivoted appropriately to collapse it against the back board to provide for a minimal profile dimension thereof.

As described above, the splint 10 preferably consists of an extremity support member 12 that is pivotally connected to back board 11 to extend appropriately therefrom, which extremity support member is formed with freely bending and pivoting elements to be positionable in an attitude to approximately conform to a person's injured extremity and after connection thereto can be locked in place to support that injured extremity. In FIG. 3, the extremity support member 12 components are shown folded upon each other at hinges 23 and 38, thereby collapsing upper and lower boards towards one another and the other elements thereon are appropriately pivoted into alignment, to provide a narrow profile thereto for stroage and convenience in transport.

Shown in FIG. 9 is a preferred rivet 17 arrangement for joining the straps 31 to lower support board 35, which rivets, it should be understood, are also preferred for securing straps 18, 20 and 20a to back board 11. Rivet 17, shown in FIG. 9, preferably includes an open ended smooth bore rivet body 17a that has a broad rounded head 17b. The rivet body 17a, as shown in section view of FIG. 9, receives a base 17c that is forced into and expands within the smooth bore thereof, to join the straps 31 to the board member 30. In FIG. 9, velcro strap ends 32 are shown connected together, linking straps 31 to illustrate maintaining the lower extremity board 30 to an injured extremity, not shown.

FIG. 5 shows extremity support member 12 broken away across the second plate 22b and the upper extremity board 25 with longitudinal elongate opening 25a shown with pivot 25 arranged therein that provides a length adjustment capability to upper extremity board 25. Shown in FIG. 5, the first and second plates 27a and 27b of the lower hinge unit 27 have been rotated to a normal angle with respect to the upper extremity board 25 and the plates themselves have been pivoted around hinge 28 to a normal angle with one another, illustrating the bending capabilities of the extremity support member 12 to show the freedom of movement capabilities thereof, whereby it can be conformed to an injured extremity.

As shown in FIG. 4, by positioning the splint 10 appropriately, such that the back board 11 wide end 15 is across a person's lower torso, it can be used for splinting a person's leg. So arranged, a required length adjustment of the extremity support member 12 is provided for by appropriately moving the pivot 26 within elongate opening 25a until a desired length is obtained, whereat pivot 26 is locked, as described. Also, shown therein, the upper and lower extremity boards 25 and 30 can be straightened with, as shown and described above, hinges 23 and 28 locked in place, and bars 38 locked to tabs 33 by nuts 36 turned thereon.

As shown and described herein, a preferred arrangement of the extremity support member 12 includes upper and lower extremity boards pivotally attached to hinge units. Though not shown, these boards and the plates of the hinge units could be contoured appropriately to conform to the shape of a person's arm or leg, and, of course, back board 11 could also be so contoured within the scope of this disclosure. Also, while straps are not shown for securing the upper extremity board 25 to a person's upper arm or thigh, it should be obvious that such straps could be so installed, also within the scope of this disclosure. Further, while it is preferred that both the single hinges 23 and 28 each have individual compressive locking capability for use in conjunction with the described bar locking, obviously a single locking arrangement only could be so employed, within the scope of this disclosure. Also, while it is preferred that tabs 33 each include a threaded bushing for receiving the bolt end 36a turned therein, threads could obviously be formed in the tab 33 material itself. Additionally, of course, a bushing could be utilized with the described nuts 49 of the pivot couplings 13, 24, 26 and 29 within the scope of this disclosure.

As shown in drawings of the present invention, the back board, first and second plates of the hinge units, and the upper and lower extremity boards of splint 10 are all preferably formed of a plastic material. However, of course, it should be understood that a metal material could be so used in the construction thereof within the scope of this disclosure.

While a preferred embodiment of the present invention in an improved universal splint has been shown and described herein, it should be understood that the present disclosure is made by way of example only, and that variations are possible without departing from the subject matter coming within the scope of the following claims, which claims I regard as my invention.

I claim:

1. An improved universal splint comprising:
   a back board that includes a transverse elongate opening therein;
   means for releasably securing said back board to a human torso;
   an upper hinge unit consisting of first and second plates that are connected together along edges thereof by a single hinge;
   a back board pivot arranged in said transverse elongate opening and connected to said first plate of said upper hinge unit;
   an upper extremity board that is connected by a pivot to said second plate of said upper hinge unit, which upper extremity board includes a center longitudinal opening formed therein;
   a lower hinge unit that, like said upper hinge unit, includes first and second plates, and includes with said first plat thereof a pivot that is arranged in said center longitudinal opening in said upper extremity board;

a lower extremity board that is connected by a pivot to the second plate of said lower hinge unit;

means for releasably locking said first and second plates of said upper and lower hinge units relative to one another;

lock means arranged with each said pivot for releasably maintaining the pivotally connected members relative to one another; and means for releasably securing said splint to a person's extremity.

2. An improved universal splint as recited in claim 1, wherein the back board is wieder across the area wherein said transverse elongate opening is formed.

3. An improved universal splint as recited in claim 1, wherein the first and second plates of the upper and lower hinge units and the upper and lower extremity boards are formed to accommodate a person's extremity thereon.

4. An improved universal splint as recited in claim 1, wherein the means for locking in place said first and second plates of each upper and lower hinge unit each consist of, hinge halves each having fingers that interdigitate and align holes formed therethrough;

a sleeve that has been internally threaded from an open end thereof that is fitted into said aligned openings formed through said fingers of each hinge; and a threaded bolt fitted also into said aligned openings that is turned into said sleeve to compress said hinge fingers together.

5. An improved universal splint as recited in claim 4, further including, tabs secured to extend at approximately normal angles inwardly from coplanar edges of the first and second plates, which tabs each have a hole formed therethrough;

thread means arranged in each said tab hole for accommodating a bolt means turned therein;

bolt means for turning in each said tab hole; and a bar arranged to extend between tabs secured to said first and second plates, which bar includes a center longitudinal opening wherethrough said bolt means are fitted prior to being turned into said tab holes.

6. An improved universal splint as recited in claim 5, wherein the thread means each consist of, a threaded bushing secured in each said tab hold.

7. An improved universal splint as recited in claim 5, wherein the bolt head outer surface is formed to facilitate its being manually turned.

8. An improved universal splint as recited in claim 1, wherein the means for locking in place said first and second plates of each upper and lower hinge unit consists of, tabs secured to extend at approximately normal angles inwardly from coplanar edges of the first and second plates, which tabs each have a hole formed therethrough;

thread means arranged in each said tab hole for accommodating a bolt means turned therein;

bolt means for turning in each said tab hole; and a bar arranged to extend between tabs secured to said first and second plates, which bar includes a center longitudinal opening wherethrough said bolt means are fitted prior to being turned into said tab holes.

9. An improved universal splint as recited in claim 8, wherein the thread means each consist of, a threaded bushing secured in each said tab hole.

10. An improved universal splint as recited in claim 8, wherein the bolt head outer surface is formed to facilitate its being manually turned.

11. An improved universal splint as recited in claim 1, wherein the pivot lock means each consist of, a large head bolt that is threaded on one end thereof and is fitted through appropriate openings formed through each said board and plate;

a large head nut formed to facilitate its manual turning on said bolt threaded end; and means for increasing the friction forces between the board and plate.

12. An improved universal splint as recited in claim 11, wherein the means for increasing the friction forces between the board and plate consists of, a washer sandwiched between said board and plate wherethrough the bolt is fitted.

13. An improved universal splint as recited in claim 1, wherein the means for releasably securing said splint to a person's extremity consist of, flexible straps that are each connected to back and extremity support boards, strap ends thereof arranged to encircle an appropriate part of the person's body; and means for releasably connecting side strap ends.

14. An improved universal splint as recited in claim 13, wherein the means for releasably connecting together ends of said straps consist of, velcro strips.

15. An improved universal splint as recited in claim 1, wherein the back board, upper and lower extremity boards, first and second plates of the upper and lower hinge units, and the hinge connections thereof are formed from a plastic material.

* * * * *